US Patent [19] 4,115,197
Queener et al.
[45] Sep. 19, 1978

[54] PROCEDURE FOR OBTAINING PENICILLIUM SPECIES MUTANTS WITH IMPROVED ABILITY TO SYNTHESIZE MYCOPHENOLIC ACID

[75] Inventors: Stephen W. Queener, Indianapolis, Ind.; Claude H. Nash, III, Audubon, Pa.

[73] Assignee: Eli Lilly and Company, Indianapolis, Ind.

[21] Appl. No.: 828,392

[22] Filed: Aug. 29, 1977

Related U.S. Application Data

[63] Continuation of Ser. No. 779,670, Mar. 21, 1977, abandoned.

[51] Int. Cl.$^2$ .......................... C12D 9/06; C12D 9/10; C12K 1/02
[52] U.S. Cl. .................................... 195/36 R; 195/30; 195/79; 195/81
[58] Field of Search .......................... 195/36 R, 30, 81

[56] References Cited

PUBLICATIONS

Wilkerson et al., ASM News, vol. 42, No. 7, p. 423 (1976).
Wilkerson et al., "Polyene-Antibiotic Resistant Mutants of Penicillium Stoloniferum: Sterol Content and Mycophenolic Acid Synthesis" presented at Apr. 10, 1976 meeting of Indiana Branch of ASM.
Muth et al., Antimicrobial Agents and Chemotherapy, vol. 8, pp. 321-327 (1975).

Primary Examiner—Lionel M. Shapiro
Attorney, Agent, or Firm—Nancy J. Harrison; Arthur R. Whale

[57] ABSTRACT

A procedure for efficiently obtaining higher mycophenolic-acid-producing mutants from mycophenolic-acid-producing strains of the genus Penicillium by selecting mutants which are resistant to polyene antibiotics.

8 Claims, No Drawings

PROCEDURE FOR OBTAINING PENICILLIUM SPECIES MUTANTS WITH IMPROVED ABILITY TO SYNTHESIZE MYCOPHENOLIC ACID

This is a continuation of application Ser. No. 779,670, filed Mar. 21, 1977, now abandoned.

BACKGROUND OF THE INVENTION

The usual practice for improving the yield of secondary metabolites produced by a microorganism involves (1) exposing the microorganism to a mutagen and (2) screening random survivors for increased titers of the secondary metabolite. The second step involves individual fermentation of each surviving isolate. This is a very expensive, time-consuming operation.

Mycophenolic acid (MPA) is a compound with several useful biological activities. It is an antiviral and antitumor agent [K. Ando et al., *J. Antibiot.* (Tokyo) 21, 649–652 (1968) and R. H. Williams et al., *J. Antibiot.* (Tokyo) 21, 463–464 (1968)]. Mycophenolic acid is also an antifungal and an antibacterial agent [K. Gilliver, *Ann. Bot.* (London) 10, 271–282 (1946) and E. Abraham, *Biochem. J.* 39, 398–408 (1945)]. Mycophenolic acid has also been reported to be useful in the treatment of psoriasis [I. S. Johnson, *Chem. Abstr.* 77:92853 (1972)].

Mycophenolic acid is produced by many species of Penicillium, e.g., *P. brevi-compactum, P. stoloniferum, P. scabrum, P. nagemi, P. szaferi, P. patus-mei, P. griscobrunneum,* and *P. viridicatum* [P. W. Clutterbuck et al., *Biochem. J.* 26, 1442–1458 (1932)]. In fact, mycophenolic acid was initially isolated from a culture of Penicillium [B. Gosio, *Riv. Igiene Sanita Pub. Ann.* 7, 825–869 (1896)].

The structure of mycophenolic acid was determined chiefly by Raistrick et al. [J. H. Birkinshaw, H. Raistrick, and D. J. Ross, *Biochem. J.* 50, 630–634 (1952)]. Mycophenolic acid was found to have the following structure:

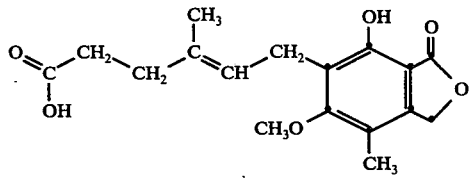

In the biosynthesis of mycophenolic acid by Penicillium species, it has been shown that both the phenolic nucleus and the seven-membered side chain of MPA are formed from acetate units (A. J. Birch et al., *J. Chem. Soc.* 1958, 369–375). The side chain of MPA arises by introduction of a $C_{15}$ terpene, presumably farnesylpyrophosphate (FPP), followed by oxidative fission at the double bond of the FPP moiety [L. Canonica et al., *J. Chem. Soc. Perkins Trans.* I. 21, 2639–2653 (1972)]. FPP also serves as a precursor of sterols (E. Heftman et al., "Biochemistry of Steroids," Reinhold Publishing Corp, New York, 1960, p. 231). Ergosterol is an important constituent of fungal membranes (D. Gottlieb, 'Functions of Sterols in Fungi' in "Morphological and Biochemical Events in Plant Parasite Interaction," S. Akai, Ed., Mochizuki Publishing Co., Omiya, Japan, 1971).

Polyene antibiotics such as, for example, nystatin, filipin, and amphotericin B are known to exert a toxic effect on fungi by binding with the ergosterol in fungal membranes [J. M. T. Hamilton-Miller, *Adv. Appl. Microbiol.* 17, 109–134 (1974)]. The primary mechanism of resistance to polyene antibiotics develops in fungi by genetic interruption of the biosynthesis of ergosterol, producing sterols with less affinity to polyene antibiotics. These sterols then produce fungal membranes with altered permeability characteristics. Another possible class of polyene-resistant mutants includes those which overproduce ergosterol, thereby detoxifying the antibiotics before they reach the membrane [W. A. Zygmunt and P. A. Tavormina, *Appl. Microbiol.* 14, 865–869 (1966)]. Two classes of polyene-resistant mutants might overproduce mycophenolic acid by overproducing FPP: (1) those in which the synthesis of FPP is normal, but synthesis of ergosterol is blocked after FPP, and (2) those which overproduce both FPP and ergosterol.

BRIEF SUMMARY

The present invention relates to a new procedure by which a population of Penicillium cells can be enriched efficiently for mutants which are better mycophenolic acid producers than their parents. This procedure involves mutating the mycophenolic-acid-producing Penicillium species, exposing the mutated population to a polyene antibiotic and screening the polyene-antibiotic-resistant mutants for mycophenolic acid production. Use of this procedure significantly reduces the time and cost ordinarily required to obtain mutants improved for mycophenolic acid titer.

DETAILED DESCRIPTION

We have discovered that increased-mycophenolic-acid-producing mutants can be obtained at a higher frequency from populations of polyene-antibiotic-resistant (PAR) mutants of Penicillium species than can be obtained from randomly selected colonies. The polyene antibiotic apparently alters the metabolism of sterol precursors (e.g. FPP) in the resistant mutants, thereby increasing titers of mycophenolic acid. Polyene antibiotics have not previously been used to alter the metabolism of FPP in fungi in order to increase titers of FPP-derived metabolites such as MPA.

The present invention relates, therefore, to a procedure for obtaining Penicillium strains which produce more mycophenolic acid than their parent strains produce. The invention significantly reduces the number of strains which must be screened in order to obtain a yield increase, in contrast to the standard procedure which involves time-consuming random screenings of mutagenized populations of Penicillium cultures.

The strains of Penicillium species useful in our procedure are those which produce mycophenolic acid and which are sensitive to polyene antibiotics. These strains are used as parental strains from which PAR strains are derived.

The first step of our procedure is to mutate the conidial populations of the Penicillium strain with a suitable mutagen, using standard procedures. Examples of suitable mutagenic agents include N-methyl-N'-nitro-N-nitroso-guanidine, ethylmethanesulfonate, nitrous acid, and ultraviolet light. When a chemical mutagen has been used, the treated cells should be washed to free the cells from the mutagen.

The second step of our procedure is to separate the polyene-antibiotic-resistant mutants. This may be carried out by a variety of techniques. A preferred method, however, is as follows: The treated cells are diluted in an appropriate suspending medium. An aliquot of the cell suspension is filtered aseptically onto a porous membrane (approximately $1 \times 10^5$ cells/membrane).

The membranes are placed on nutrient pads saturated with a liquid medium and are incubated overnight at 20°–30° C. to allow for expression. The membranes then are transferred to other nutrient pads saturated with the same medium but incorporated with a range of concentrations of a polyene antibiotic, such as nystatin or filipin. Examples of the range of concentrations used are: 10–100 mcg/ml of nystatin and 5 to 50 mcg/ml of filipin. The membranes are incubated at about 20°–25° C. until pinpoint colonies are observable. Clones are isolated from membranes supporting no more than 20 clones/membrane. These strains are sustained on slants of liquid complex medium solidified with 1.5% agar and are later re-evaluated to confirm the level of resistance to the specific polyene antibiotic from which they were isolated. Second-generation strains are derived from resistant strains that were mutated again and treated as earlier described, thus acquiring mutants resistant to even higher concentrations of the polyene antibiotics.

The PAR mutants thus obtained are then evaluated for mycophenolic acid production, using standard procedures. For example, the mutants are maintained on slants consisting of a complex liquid medium solidified with 1.5% agar. A standard volume of cells thus maintained is scraped into a defined fermentation medium [(W. L. Muth et al. Antimicrob, Agents Chemotherap. 8, 321 (1975)] and fermented 4–6 days, incubating at about 25° C. on a rotary shaker at about 250–285 rpm. Incubated whole broth is adjusted to pH 8 to dissolve the MPA. Buffered samples are mixed with chloroform at a ratio of 1 to 10. The chloroform phase is separated and read at 304 nm on an ultraviolet spectrophotometer.

High titers of mycophenolic acid are confirmed by standard methods of isolation and characterization from subsequent fermentations.

This invention also relates to a method of producing mycophenolic acid with a strain of *Penicillium stoloniferum* which was developed by this new procedure. The parent strain used to develop this improved strain was *P. stoloniferum* NRRL 859. Both *P. stoloniferum* NRRL 859 and the improved strain are available to the public from the Northern Regional Research Center, Agricultural Research Service, U.S. Dept. of Agriculture, 1815 N. University Street, Peoria, Ill. 61604. The improved strain is available to the public under the number NRRL 11078.

The culture medium used to grow the improved strain, *P. stoloniferum* NRRL 11078, can be any one of a number of media. Media commonly used in the production of mycophenolic acid are known to those skilled in the art [see, for example, W. L. Muth et al., Antimicrob. Agents Chemotherap. 8, 321–327 (1975); R. H. Williams et al., Antimicrobial Agents Chemotherap. 1968, 229–233; and British Pat. Nos. 1,158,387 and 1,157,099]. Appropriate culture media contain assimilable sources of carbon, nitrogen, and inorganic salts. Fermentation is carried out under aerobic fermentation conditions, using standard procedures, until a substantial amount of mycophenolic acid is produced. To determine peak mycophenolic acid production, MPA may be monitored by a variety of methods. A preferred method involves a simple separation procedure and use of the ultraviolet absorption maximum exhibited by mycophenolic acid at 304 nm, as earlier described.

In order to illustrate more fully the operation of this invention, the following example is provided.

EXAMPLE 1

*Penicillium stoloniferum* strain NRRL 859 was used as the parental strain from which the polyene-antibiotic-resistant mutants were derived. Conidial populations of 2 to 3 × $10^6$ cells/ml were mutated for 10 minutes with N-methyl-N'-nitro-N-nitrosoguanidine at a final concentration of 1.0 mg/ml in 0.05 M tris (hydroxymethyl) aminomethane (Tris, Fisher Scientific) buffer-0.05 M maleic acid, pH 8.0. Approximately 90% kill was achieved by this procedure. Treated cells were washed free of the mutagen with a saline-Tween 80 [polyoxyethylene (20) sorbitan mono-oleate] solution. The washed cells were diluted in 30 ml of suspending medium having the following composition:

| Ingredient | Amount |
|---|---|
| NaCl | 0.85% |
| Tween 80 | 0.02% |
| $K_2HPO_4$ | 0.35% |
| Deionized water; pH adjusted to 6.5 with concentrated HCl | |

Portions of the suspended-cell solution (2.5 ml) were filtered aseptically onto cellulose ester membrane filters (Millipore Corp., Bedford, Mass. 01730; diameter 47-mm; pore size 0.45 μ; #HAWG04700; approximately 1 × $10^5$ cells/membrane).

The prepared membranes were placed on absorbent cellulosic pads (Millipore Corp, #AP10-047S0) saturated with 2 ml of liquid complex medium having the following composition:

| Ingredient | Amount (5) |
|---|---|
| Glucose | 1.00 |
| Casein, acid-hydrolyzed | 0.50 |
| Yeast extract | 0.20 |
| $NH_4Cl$ | 0.10 |
| $KH_2PO_4$ | 0.54 |
| $MgSO_4 \cdot 7H_2O$ | 0.04 |
| $CaCO_3$ | 0.04 |
| Tap water; pH adjusted to 6.5 with 50% NaOH prior to sterilizing | |

The membranes were incubated on the pads overnight at 23° C. to allow for expression. The membranes then were transferred to other nutrient pads saturated with the same complex medium but incorporated with a range of concentrations of filipin and nystatin. The following concentrations were employed:

filipin 10–25 mcg/ml
nystatin 20–70 mcg/ml

The membranes were incubated at 23° C. until pinpoint colonies were observable. Clones were isolated from those membranes supporting no more than 20 clones/membrane. These strains were sustained on slants of the same liquid complex medium solidified with 1.5% agar and were later reevaluated to confirm the level of resistance to the specific polyene antibiotic from which they were isolated. Forty-five PAR strains were selected. Twenty one of these strains were evaluated for MPA production in shake flasks. One of these strains, NRRL 11078, was resistant to 15 mcg/ml filipin and produced significantly more mycophenolic acid than the parent strain in three fermentation test, as shown in Table I.

TABLE I

| | Maximal Mycophenolic Acid Titer (mg/ml) | | |
| --- | --- | --- | --- |
| | Parent Strain NRRL 859 | Mutant Strain NRRL 11078 | Fermentation Duration (Days) |
| Test 1 | 1.23 | 1.85 | 6 |
| Test 2 | 1.78±.13 | 1.96±03 | 6 |
| Test 3 | 0.69±.08 | 0.87±.09 | 4 |

We claim:

1. A method for efficiently obtaining higher mycophenolic-acid-producing strains of Penicillium, which consists of mutating a mycophenolic-acid-producing Penicillium strain, exposing the mutated population to a polyene antibiotic and screening the polyene-antibiotic-resistant strains for mycophenolic acid production.

2. The method of claim 1 wherein the polyene antibiotic used is filipin.

3. The method of claim 2 wherein the concentration of filipin is from about 5 to about 50 mcg/ml.

4. The method of claim 1 wherein the polyene antibiotic used is nystatin.

5. The method of claim 4 wherein the concentration of nystatin is from about 10 to about 100 mcg/ml.

6. The method of claim 1 wherein the mycophenolic-acid-producing strain is *Penicillium stoloniferum*.

7. The method of claim 6 wherein the *Penicillium stoloniferum* strain is NRRL 859.

8. The method of producing mycophenolic acid which comprises cultivating *Penicillium stoloniferum* NRRL 11078 in a culture medium containing assimilable sources of carbon, nitrogen and inorganic salts under submerged aerobic fermentation conditions until a substantial amount of mycophenolic acid is produced.

* * * * *